Figure 1:
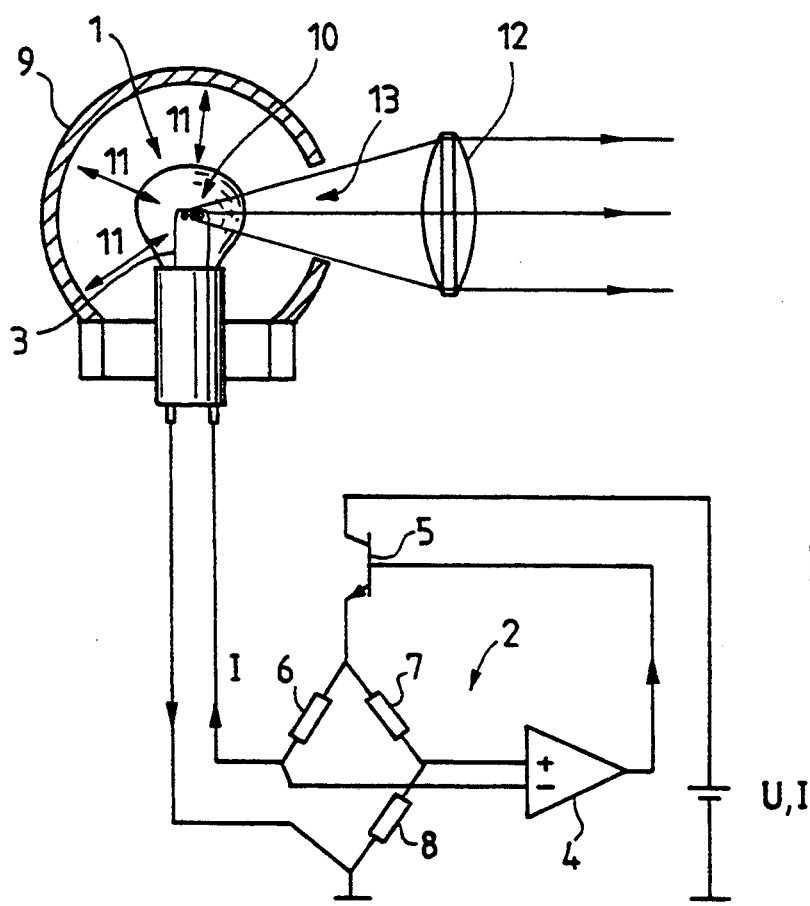

United States Patent [19]

Keränen

[11] Patent Number: 5,383,101
[45] Date of Patent: Jan. 17, 1995

[54] DEVICE FOR GENERATING RADIATION

[75] Inventor: Heimo Keränen, Oulu, Finland

[73] Assignee: Rautaruukki Oy, Oulu, Finland

[21] Appl. No.: 137,157

[22] PCT Filed: Mar. 19, 1993

[86] PCT No.: PCT/FI93/00103

§ 371 Date: Oct. 26, 1993

§ 102(e) Date: Oct. 26, 1993

[87] PCT Pub. No.: WO93/19351

PCT Pub. Date: Sep. 30, 1993

[30] Foreign Application Priority Data

Mar. 20, 1992 [FI] Finland .................. 921220

[51] Int. Cl.⁶ .................. F21V 21/30; G01J 1/00
[52] U.S. Cl. .................. 362/35; 362/284;
362/321; 250/504 R; 250/339.06
[58] Field of Search .................. 362/35, 280, 282, 284,
362/321; 374/131; 250/351, 504 R, 339.06;
359/235

[56] References Cited

U.S. PATENT DOCUMENTS

| | | | |
|---|---|---|---|
| 3,449,571 | 6/1969 | Hoerman et al. | 250/339.03 X |
| 3,957,377 | 5/1976 | Hutchinson | 359/235 X |
| 4,009,966 | 3/1977 | Craig | 356/123 |
| 4,275,327 | 6/1981 | Walsh | 313/111 |
| 4,346,324 | 8/1982 | Hirschfeld | 313/111 |
| 4,429,225 | 1/1984 | Fumoto et al. | 250/339.06 X |
| 4,644,899 | 2/1987 | Glaus | 250/504 R X |
| 4,790,669 | 12/1988 | Christensen | 374/131 |

FOREIGN PATENT DOCUMENTS 4002630 8/1991 Germany .
WO9007697 7/1990 WIPO .
WO9014580 11/1990 WIPO .

Primary Examiner—Ira S. Lazarus
Assistant Examiner—Thomas M. Sember
Attorney, Agent, or Firm—Sughrue, Mion, Zinn, Macpeak and Seas

[57] ABSTRACT

The invention relates to a device for generating radiation, which device comprises an electrically operated radiation source (1), a cap-like reflector means (9), which reflector means (9) is positioned around the radiation source (1). The reflector means (9) comprises an opening (13) for directing radiation out of the reflector means (9) towards a collecting optics (12) positioned in the vicinity of the opening (13). The device comprises a rotatable modulator means (15) including interrupting means (16 and 17) for modulating the radiation coming from the radiation source (1). The modulator means (15) is cup-like, comprising a bottom portion (18a), at which the modulator means (15) can be rotated, and a substantially circular wall portion (18b), which wall portion (18b) comprises the interrupting means (16 and 17). The modulator means (15) is positioned around the cap-like reflector means (9) in such a way that, when rotating the modulator means (15), the wall portion (18b) with its interrupting means (16 and 17) is arranged to rotate around the cap-like reflector means (9) in front of the opening (13).

10 Claims, 2 Drawing Sheets

DEVICE FOR GENERATING RADIATION

The invention relates to a device for generating radiation, which device comprises an electrically operated radiation source to be connected to a power source, a means for regulating the current of the radiation source and an at least partly curvilinearly symmetric cap-like reflector means, which reflector means is positioned round the radiation source in such a way that the radiation source is situated mainly in the centre of curvature of the reflector means or in the vicinity thereof and the cap-like reflector means surrounds the radiation source along a wide sector, the cap-like reflector means comprising an opening for directing radiation out of the reflector means towards a collecting optics positioned in the vicinity of the opening and the size of the opening being arranged to limit the outcoming radiation mainly only to the collecting optics, which device additionally comprises a modulator means rotatable about its rotating axis and including interrupting means for modulating the radiation coming from the radiation source outside the reflector means by interrupting the propagation of the radiation.

A device according to the invention can be used for instance for generating infrared radiation in various spectroscopic measuring devices, by which is measured e.g. on various surfaces how thick a film of impurities or slushing oil or some other substance there is on the surface. It is important to measure the thickness of the film in order to know for painting or otherwise treating the surface, whether the surface shall be cleaned before the painting.

The measuring devices also need a device solution for generating radiation. The measuring devices are based on the fact that the device emits infrared radiation, which is partially reflected back from the surface to be measured. How much reflection occurs, depends on the thickness of the film on the surface and on the properties of the film. The infrared radiation reflected from the surface is measured into a measuring device through optics by means of a detector means.

In measuring devices, a measurement is carried out in several wavelength channels, which makes certain demands on the electrically operated radiation source and associated device solutions, namely that the shape of the spectrum of radiation emitted by the radiation source should remain constant within the area of the object to be measured. The radiation source generally used in infrared spectroscopy is a bulb, the shape of the radiation spectrum of which depends on the temperature of the filament of the bulb. Within the spectrum area, the point of the highest amplitude of a spectrum graph moves somewhat towards a smaller wavelength when the temperature of the filament rises. Infrared spectroscopy presupposes that relative changes in the spectrum would be of pro mille order only, but that is often not the case, depending expressly on changes in the temperature of the radiation source.

For stabilizing the temperature of the filament, a regulating means is generally used, by which the current of the filament can be regulated. Resistance feedback can, for instance, be used as a regulating means, by which feedback the regulating means reduces, at rising temperature of the radiation source and at simultaneously rising resisting power of the filament of the radiation source, the current/voltage of the radiation source, which decreases the temperature of the radiation source. A problem with the realization of the radiation source is also that different parts of the filament itself have different temperatures, which is caused by the fine structure and the radiation balance of the filament compared with the surroundings. In spectroscopic measurements, radiation energy of the radiation source is collected by lenses or mirrors, which direct the radiation energy of the bulb from different parts of the filament in different directions, on account of which the shape of the radiation spectrum varies at an object lighted by optics, depending on which part, or practically, which part with which temperature of the filament is in question.

Reflector means have been used in connection with radiation sources already earlier. U.S. Pat. No. 4,808,825 discloses a liquid analyzer operating within the infrared area, in which analyzer a reflector means is positioned with respect to the radiation source in such a way that the radiation source will be situated at the middle axis of the reflector means fixed on the reflector means. This structure is suitable for directing radiation, but not for improving temperature properties of the radiation source, e.g. for stabilizing the temperature of the radiation source. A respective solution is set forth in U.S. Pat. No. 3,690,773. U.S. Pat. No.4,790,669 discloses a spectrometer, in which a light source and a rotating shutter are used for distributing radiation to various detectors. The above solutions show deficiencies at the stabilization of the temperature properties of the radiation source.

Solutions have been presented for improving the temperature properties of a radiation source. U.S. Pat. No. 4,346,323, for instance, discloses a structure in which a spherically symmetric reflector cap provided with a small opening is positioned round a radiation source. A structure of corresponding type is also disclosed in U.S. Pat. No. 4,275,327, as far as the shape and positioning of the reflector cap are concerned. WO Patent 90/14580 and German Patent 4002630 describe devices for generating radiation, in which devices a radiation source is partly surrounded by a curved reflector means. The purpose of improving the temperature properties of the radiation source is, in addition to the other purposes, to stabilize the temperature of the radiation source. In these known solutions, the opening for the outlet of the radiation existing in the reflector cap constitutes a problem. The known solutions, mostly being stationary spectrometric devices, do not disclose sufficiently small sized compact solutions with sufficiently good properties for performing a modulation of radiation either. As to the above publications and PCT publication WO 90/07697, only the latter one discloses a modulator means, which is, however, a disc placed far from the radiation source, which disc comprises holes and solid portions between them, which interrupt, i.e. modulate, radiation. In this known solution, the efficiency of the modulation remains partly deficient because of the positioning of the modulator, and the device of the solution will be big-sized, which again causes problems particularly in connection with portable spectroscopic measuring devices.

The object of the present invention is to set forth a novel device for generating radiation, which device avoids the problems associated with the known solutions.

This object is achieved by means of a device according to the invention, which is characterized in that the modulator means is cup-like and comprises a bottom portion, at which the modulator means can be rotated, and a substantially circular wall portion, which wall portion comprises interrupting means, and that the cup-like modulator means is positioned round the cap-like reflector means in such a way that, when rotating the modulator means, the wall portion together with its interrupting means are arranged to rotate along a substantially circular periphery round the cap-like reflector means.

A device according to the invention is based on the idea that the radiation source, the cap-like reflector means and the modulator means are integrated into a homogenous unity.

Several advantages are achieved by means of the device according to the invention. The modulator means positioned round the cap-like reflector means improves further the temperature properties of the radiation source, because the modulator means, when interrupting radiation, also covers the opening of the reflector cap. By means of the modulator means of the invention, a compact, small-sized, reliable and light device solution is achieved especially for portable measuring devices intended for hard field conditions. The efficiency of the modulation will also improve.

Figure 2:
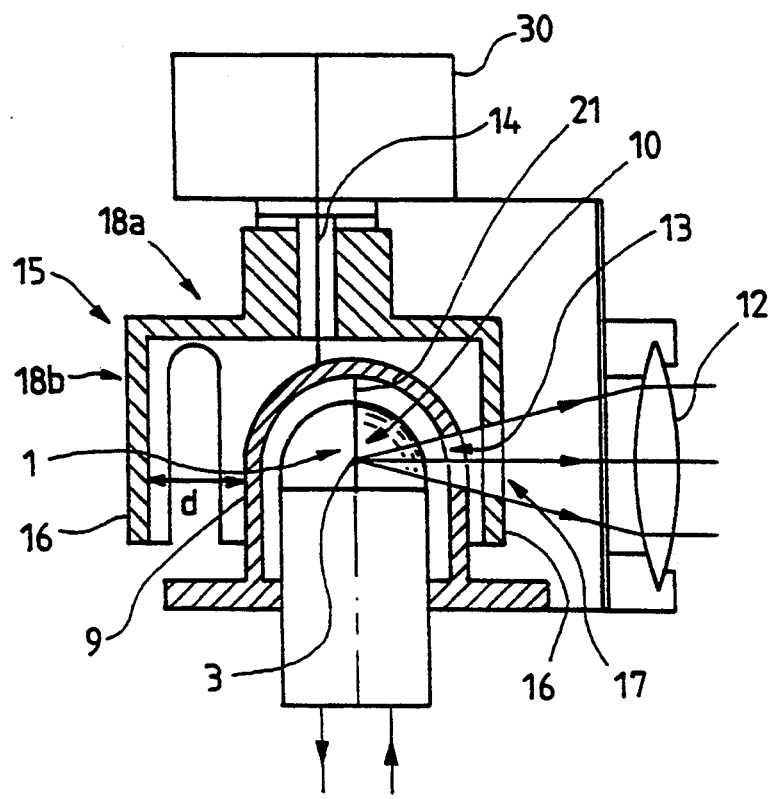
Figure 3:
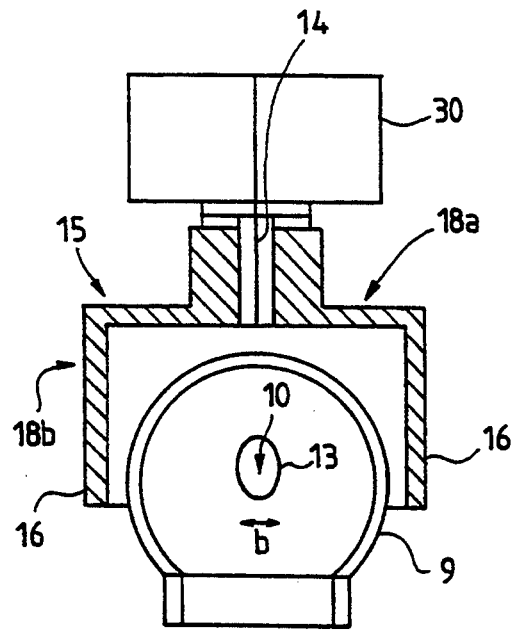
Figure 4:
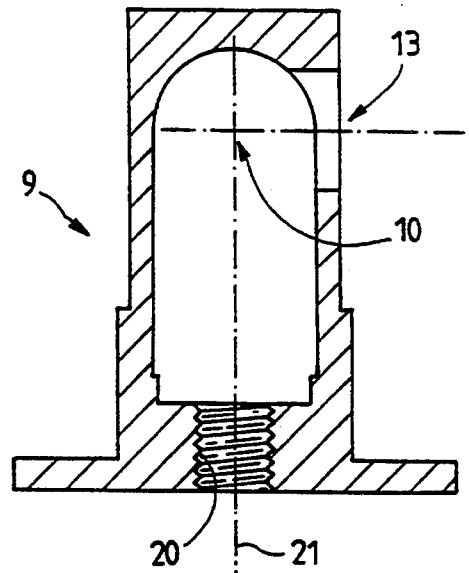
Figure 5:
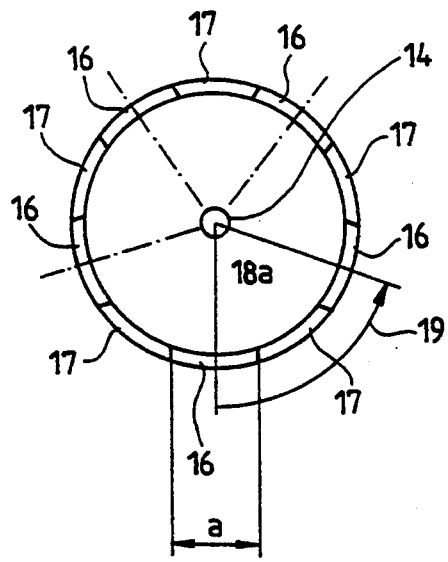
Figure 6:
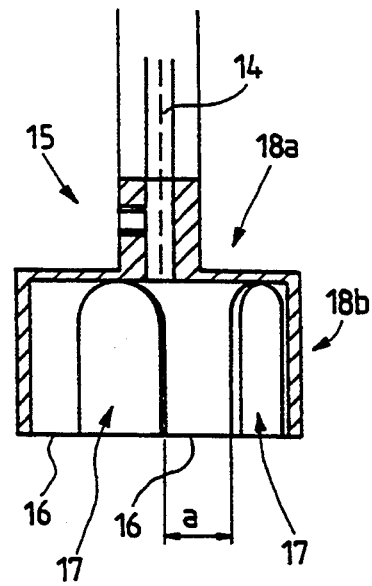

The invention will be explained in greater detail in the following with reference to the enclosed drawings, in which FIG. 1 shows a general view of a device according to the invention schematically, FIG. 2 shows the device of the invention perpendicularly from the side with respect to the centre line of a light to be obtained out of a reflector means, FIG. 3 shows the device of the invention in the direction of the centre line of a light ray to be obtained out of the reflector means, FIG. 4 shows a cross-section of the reflector means, FIG. 5 shows a cup-like modulator means in the direction of its rotation axis, FIG. 6 shows the cup-like modulator means perpendicularly from the side with respect to the direction of its rotation axis.

According to FIG. 1, a device for generating radiation comprises an electrically operated radiation source 1, which is connected to a means 2 for current regulation. The radiation source 1 can be for instance a bulb comprising a filament 3. The radiation source 1 is connected to a voltage/current source U through the regulating means 2. According to FIG. 1, for instance, the regulating means 2 can be realized by means of resistance feedback. The regulating means 2 comprises e.g. an operational amplifier 4, a transistor 5 and resistances 6, 7 and 8. In practice, the filament 3 also forms one resistance, the resisting power of which depends on the temperature of the filament 3 or, more widely, on that of the radiation source 1. When the resisting power of the radiation source 1 or, to be precise, that of the filament 3, rises, the regulating means 2 carries out a voltage distribution between the various resistances 6 to 8 and the filament 3 and reduces a current I going to the radiation source 1, whereby the temperature of the radiation source 1 falls. Respectively, when the resisting power of the radiation source 1, or more precisely, that of the filament 3, falls at a fall of the temperature, the regulating means 2 permits a higher current to go to the radiation source 1, i.e. to the filament 3 of the bulb. The term regulating means designated 2 shall be understood widely, which means that many other solutions than resistance feedback can serve as the regulating means.

The regulating means can be for instance a simple limiter, by which is set a certain limit value in advance, by which the current going to the radiation source is limited in such a way that the temperature of the radiation source is definitely not to rise too high.

The device also comprises a reflector means 9. In order to stabilize the temperature of the radiation source 1, the reflector means 9 is positioned round the radiation source 1 in such a way that the radiation source 1 is situated mainly in the centre of curvature 10 of the reflector means 9 or in the immediate vicinity thereof, whereby radiation can be reflected back to the radiation source 1 by the reflector means 9. In FIG. 1, the centre of curvature 10 of the reflector means 9 remains in the region of the middle of the filament 3. Arrows 11 indicate the reflection of radiation back to the radiation source 1. The reflection of radiation back to the radiation source 1 makes the temperature and simultaneously the resisting power of the radiation source 1 rise, but then the regulating means 2 decreases the current coming to the bulb, because of which the temperature falls. In this manner it is possible to stabilize the temperature of the radiation source 1 efficiently. If the radiation source 1 is a bulb, then the filament is positioned in the centre of curvature of the reflector means.

Outside the reflector means 9 is positioned a collecting optics 12, i.e. a collecting lens, which collimates light rays, viz. makes them parallel with each other. As the collecting optics 12 can serve an optical means consisting of one or several lens(es) or mirror(s) or a combination of both.

The device is realized in such a way that the reflector means 9 is cap-like and surrounds the radiation source 1 along an at least partly spherical or otherwise curvilinearly symmetric sector of the size of at least 180°. Then the radiation energy started from the radiation source 1 can be directed very efficiently from different directions back to the radiation source 1, i.e. to the filament 3 of the bulb. FIG. 1 shows the reflector means 9 in cross-section, and therefore only the outer and inner edges of the cap-like reflector means 9 can be seen in FIG. 1. The cap-like reflector means 9 comprises an opening 13, through which light rays can be directed forward to the collecting optics 12. The device for generating radiation is one partial section of a bigger unity, e.g. a spectrometer, and thus, in practice, the light to be obtained from the collecting optics 12 is directed further through additional optics or directly to the object to be measured, from which a part of the light is reflected, which part of the light is directed to a detector means (not shown).

Consequently, the reflector means 9 comprises the opening 13 for directing radiation out of the reflector means 9 towards the collecting optics 12 positioned in the vicinity of the opening 13, and then the size of the opening 13 is arranged to limit the outcoming radiation only to the collecting optics 12. In practice, the size of the opening 13 is determined on the basis of the focal distance and the diameter of the collecting optics 12.

The radiation reflected back is partly absorbed by the filament and changed into heat energy, increasing the temperature of the filament. The unabsorbed part of the radiation is either reflected further to the cap reflector 9 or led to the collecting optics 12 through the opening 13 of the cap 9. Consequently, the reflector cap homogenizes temperature differences of the filament.

The reflector means 9, i.e. the reflector cap, positioned round the radiation source can also cover more than the above-mentioned 180°, for instance over 270°. According to FIGS. 1 and 3, the reflector cap can then be spherical or, according to FIG. 2, its upper part can be partly spherical and its lower part can deviate from the spherical form and be e.g. tubular.

In spectrometric measuring devices, the light obtained from the radiation source 1 is interrupted, i.e. modulated. The modulation frequency depends on how often the interruption occurs. According to FIGS. 2 and 3, a device generating modulated radiation additionally comprises a modulator means 15 rotatable round its rotating axis 14 and including interrupting means 16, 17 for modulating the radiation coming from the radiation source outside the reflector means 9 by interrupting the propagation of the radiation. The modulator means 15 is rotated round its rotation axis 14 by a motor 30. The rotational speed of the motor 30 depends on the desired interrupting or modulation frequency.

When the reflector means 9 according to the invention is cap-like and surrounds the radiation source 1 extensively, the modulator means 15 can be realized in a very usable novel manner by a method saving space round the reflector means 9 and improving the efficiency of the modulation. Then the modulator means 15 is cup-like and comprises a bottom portion 18a, at which the modulator means 15 can be rotated round its rotating axis 14 by the motor 30, and a substantially circular wall portion 18b, which wall portion 18b comprises the interrupting means 16 and 17. Then the cup-like modulator means 15 is positioned round the cap-like reflector means 9 in such a way that, when rotating the modulator means 15, the wall portion 18b together with its interrupting means 16 and 17 are arranged to rotate along a substantially circular periphery 19 round the cap-like reflector means 9. Referring to the FIGS. 2, 3, 5 and 6, the modulator means 15 is realized in a preferred embodiment of the invention in such a way that, when rotating past the opening 13 of the reflector means 9, each wall area 16 (5 in number), i.e. branch, of the wall portion 18b of the modulator means 15 covers the whole opening 13 and thus prevents a propagation of an actual light ray to the collecting optics 12 and, on the other hand, also prevents a propagation of stray light. In a preferred embodiment, the interrupting means 16 and 17 included in the wall portion 18b have been performed in such a way that the interrupting means 16 and 17 included in the wall portion 18b of the modulator means 15 comprise several openings and/or recesses 17 formed in the wall portion 18b at substantially equal distances and wall areas 16 to separate them. Then the wall portion 18b of the modulator means 15 resembles a branch and comprises alternating wall areas 16, i.e. branches, and openings between them, i.e. open places 17. The breadth a of each wall area 16 shall be preferably broader than or equal to the breadth b of the opening 13 of the reflector means 9, due to which the modulator means interrupts radiation efficiently. A suitable rotational speed for the modulator means 15 to be rotated by a motor is for instance 3000 r/min, whereby the modulation or interrupting frequency of the modulator means 15 provided with five pairs of branches/open places 16, 17 is 15,000 times per minute, i.e. 250 Hz. The wall areas, i.e. branches 16, and the open places 17 are positioned at substantially equal distances along the periphery 19 of the wall portion 18b of the modulator means 15, due to which the interruption occurs evenly.

Referring to FIGS. 2 and 3, the cup-like modulator means 15 extends in a preferred embodiment of the invention to a curved sector surface of at least 180 degrees round the centre of curvature of the reflector cap. Then the cup-like modulator means 15 encloses sufficiently within itself the cap-like reflector means 9 and the modulator means 15 protects the reflector means 9 and the radiation source 1 at the same time. In a preferred embodiment, the cup-like modulator means 15 is positioned between the reflector means and the collecting lens 12 according to the FIGS. 2 and 3, due to which the modulator means can be arranged as close to the radiation source as possible, and then, in addition to the opening 13 of the radiation source 1, also the openings or recesses 17 included in the wall portion 18b of the modulator means 15 serve as a means limiting the radiation beam to the collecting lens 12. In a preferred embodiment, the collecting lens is positioned in the immediate vicinity of the cup-like modulator means, in which case the device according to the invention forms a compact device generating modulated collimated radiation.

Referring to the FIGS. 5 and 2, the inner surface of the wall portion 18b of the cup-like modulator means 15 is substantially circular in a preferred embodiment, due to which the curved inner surface, or in practice, the inner surfaces of the branches or wall areas 16, direct radiation more accurately back to the reflector cap 9 by interrupting the radiation. Moreover, the cup-like modulator means having a substantially circular inner surface is rather easy to manufacture.

In a preferred embodiment of the invention, the distance between the modulator means 15 and the cap-like reflector means 9 measured at the opening 13 of the reflector means 9 is shorter than a distance d between the modulator means 15 and the reflector means 9 measured at the opposite side of the reflector means 9. One embodiment of the solution in question can most preferably be realized according to FIG. 2, in which the modulator means 15 is positioned round the reflector cap 9 in such a way that the rotating axis 14 of the modulator means 15 and a centre axis 21 of the reflector cap 9 are not situated in line, due to which the reflector cap 9 is positioned unsymmetrically within the modulator cup 15. Then the distance between the modulator means 15 and the reflector means 9 at the opening 13 of the reflector means 9 can be made short and, on the other hand, the length of the periphery 19 of the wall portion 18b of the modulator means 15 can be made big enough for providing a sufficiently high modulation frequency by means of several interrupting means 16 and 17, which means in practice a sufficient amount of pairs of branches and open places.

In one preferred embodiment of the invention, the reflector means 9 is manufactured of aluminium. Aluminium is an advantageous material and has good reflectivity properties. Further, in one preferred embodiment, the reflector means 9 consists substantially of a one-piece body according to FIG. 4. A one-piece body, such as a casting, is a very usable structure for the cap-like reflector means and makes it possible to achieve good reflectivity properties and simplifies the structure of the device. If the reflector means 9 has been made to a one-piece body, then the reflector means 9 comprises in a preferred embodiment a fastening part 20, through which the radiation source can be arranged to be fastened to the reflector means 9. The reflector means 9 acts then simultaneously as a fastening frame for the radiation source 1 and, on the other hand, the realization of the reflector means 9 is compact and, especially in portable measuring devices, resistant to even hard use. The fastening part 20 is preferably a thread part according to FIG. 4 or a fastening part to be fastened by compression according to FIG. 1.

FIG. 5 shows the modulator means 15 in the direction of its rotating axis 14. The periphery of the wall portion 18b of the modulator means is circular and comprises alternating wall areas 16 and open places 17, viz. openings and/or recesses. The structure of the cup-like modulator means 15 and its wall portion 18b are to be seen more distinctly from FIG. 6, which structure is an especially usable solution in connection with the cap-like reflector means positioned round the radiation source. Consequently, the modulator means 15 is then positioned round the reflector means according to FIGS. 2 and 3.

Though the invention has been described above referring to the examples according to the enclosed drawings, it is clear that the invention is not restricted to them, but it can be modified in many ways within the scope of the inventive idea set forth in the enclosed claims.

I claim:

1. A device for generating radiation, which device comprises an electrically operated radiation source (1) to be connected to a power source (U, I), a means (2) for regulating a current of the radiation source (1) and an at least partly curvilinearly symmetric cap-like reflector means (9), which reflector means (9) is positioned round the radiation source (1) in such a way that the radiation source (1) is situated mainly in a centre of curvature (10) of the reflector means (9) or in the vicinity thereof and the cap-like reflector means surrounds the radiation source along a wide sector, the cap-like reflector means (9) comprising an opening (13) for directing radiation out of the reflector means (9) towards a collecting optics (12) positioned in the vicinity of the opening (13) and the size of the opening (13) being arranged to limit the outcoming radiation mainly only to the collecting optics (12), which device additionally comprises a modulator means (15) rotatable about a rotating axis thereof and including interrupting means (16 and 17) for modulating the radiation coming from the radiation source (1) outside the reflector means (9) by interrupting the propagation of the radiation, characterized in that the modulator means (15) is cup-like and comprises a bottom portion (18a), at which the modulator means (15) can be rotated, and a substantially circular wall portion (18b), which wall portion (18b) comprises interrupting means (16 and 17) and that the cup-like modulator means (15) is positioned round the cap-like reflector means (9) in such a way that, when rotating the modulator means (15), the wall portion (18b) together with its interrupting means (16 and 17) are arranged to rotate along a substantially circular periphery (19) round the cap-like reflector means (9).

2. A device according to claim 1, characterized in that the interrupting means (16 and 17) included in the wall portion (18b) of the modulator means (15) comprise several open places (17), such as openings and/or recesses, formed in the wall portion (18b) at substantially equal distances and wall areas (16) to separate them.

3. A device according to claim 2, characterized in that the breadth (a) of the wall areas (16) is at least equal to the breadth (b) of the opening (13) of the reflector means (9).

4. A device according to claim 1, characterized in that the cup-like modulator means (15) extends to a sector surface of at least 180 degrees round the centre of curvature (10) of the reflector cap.

5. A device according to claim 1, characterized in that the cup-like modulator means (15) is positioned between the reflector means (9) and the collecting optics (12).

6. A device according to claim 1, characterized in that the collecting optics (12) is positioned in the immediate vicinity of the cup-like modulator means (15).

7. A device according to claim 1, characterized in that an inner surface of the wall portion (18b) of the cup-like modulator means (15) is substantially circular.

8. A device according to claim 1, characterized in that the distance between the modulator means (15) and the cap-like reflector means (9) measured at the opening (13) of the reflector means (9) is shorter than the distance between the modulator means (15) and the reflector means (9) measured at an opposite side of the reflector means (9).

9. A device according to claim 1, characterized in that the modulator means (15) is positioned around the reflector cap (9) in such a way that the rotating axis (14) of the modulator means (15) and a centre axis (21) of the reflector cap (9) are not situated in line.

10. A device according to claim 1, characterized in that the wall portion (18b) of the cup-like modulator means (15) forms an angle of substantially 90 degrees with respect to the bottom portion (18a) of the modulator means (15).

* * * * *